(12) United States Patent
Melching et al.

(10) Patent No.: US 7,556,779 B2
(45) Date of Patent: *Jul. 7, 2009

(54) CLIMATIC CABINET

(75) Inventors: Achim Melching, Langenselbold (DE); Markus Doschek, Obertshausen (DE); Christian Kern, Freigericht (DE); Olaf Brömsen, Mörfelden-Walldorf (DE)

(73) Assignee: Thermo Electron LED GmbH, Langenselbold (DE)

( * ) Notice: Subject to any disclaimer, the term of this patent is extended or adjusted under 35 U.S.C. 154(b) by 896 days.

This patent is subject to a terminal disclaimer.

(21) Appl. No.: 10/767,494

(22) Filed: Jan. 30, 2004

(65) Prior Publication Data
US 2004/0207303 A1    Oct. 21, 2004

(30) Foreign Application Priority Data
Feb. 1, 2003    (DE) .............................. 103 04 012

(51) Int. Cl.
*B01L 9/00* (2006.01)
(52) U.S. Cl. .................................................. 422/104
(58) Field of Classification Search .................. 422/104
See application file for complete search history.

(56) References Cited

U.S. PATENT DOCUMENTS 6,129,428 A * 10/2000 Helwig et al. ............... 312/114
6,536,859 B1 * 3/2003 Bathe .......................... 312/305
2002/0131895 A1   9/2002 Gjerdingen et al. ........... 422/64
2004/0115101 A1 * 6/2004 Malin ......................... 422/104

FOREIGN PATENT DOCUMENTS

| DE | 19952651 | 10/1999 |
| EP | 1155743 | 5/2001 |
| EP | 1 155 743 | 11/2001 |
| WO | WO 02/059251 | * 8/2002 |

* cited by examiner

*Primary Examiner*—Walter D Griffin
*Assistant Examiner*—Bobby Ramdhanie
(74) *Attorney, Agent, or Firm*—Baker & Hostetler LLP

(57) ABSTRACT

The invention is relative to a climatic cabinet with a door, a utilization space, a specimen storage device, an inner transport device and a transfer opening. A buffer specimen storage device and an outer transport device are arranged on the outside in front of the transfer opening. The outer transport device establishes a transport connection between the buffer specimen storage device and the transfer opening by which a specimen can be brought between the buffer specimen storage device and the inner transport device. The invention has the advantage that the dwell time of the blade in an area with outside temperature is restricted to a minimum, as a result of which an ice-free transfer of specimen slides can be carried out even given a high transfer frequency and great differences of temperature and of atmospheric moisture.

19 Claims, 4 Drawing Sheets

CLIMATIC CABINET

FIELD OF THE INVENTION

The invention pertains to a climatic cabinet with a door, a utilization space, at least one specimen slide storage device, at least one inner transport device and at least one transfer opening.

BACKGROUND OF THE INVENTION

Such a climatic cabinet is known from EP-A2-1155743. A common application is the temporary storage of specimen slides, typically so-called microtiter plates (MTP), under given climatic conditions for purposes of research and use in industrial manufacture. Such climatic cabinets are provided with a relatively large door that make possible a spacious entrance to the utilization space. However, since an undesired climatic change and the formation of frost in the utilization space if the inner temperature is low unavoidably take place when the door is opened, it is only provided for maintenance and cleaning and the like of the utilization space. Placing and removing the specimen slides therefore takes place individually with the aid of an automatic transfer device via a small transfer opening protected by the door. During this procedure the specimen slide is transported on a blade through the transfer opening. A lift with a horizontally pivotable aim cooperates with a carriage and establishes the connection to the individual storage locations of the specimen slides. Transfer device, lift and pivot arm are designated here together as an inner transport device.

A precipitation of ambient moisture that accumulates and results in the formation of ice on the blade occurs on account of the higher outside temperature when specimen slides are frequently moved in and out at low temperatures in the utilization space, e.g., in the range of −20° C. and the blade must correspondingly be frequently moved from the inside to the outside.

SUMMARY OF THE INVENTION

The invention therefore has the problem of devising a climatic cabinet of the initially cited type in which an ice-free transfer of specimen slides can be carried out even given a high transfer frequency and great differences of temperature and of atmospheric moisture.

This problem is solved in that a buffer specimen storage device and an outer transport device are arranged outside the transfer opening and in that the outer transport device establishes a transport connection between the buffer specimen storage device and the transfer opening by which a slide can be moved between the buffer specimen storage device and the inner transport device.

The invention has the advantage that the dwell time of the blade in an area with outside temperature is restricted to a minimum.

In a preferred further refinement of the invention the operating convenience is increased in that the buffer specimen storage device comprises a plurality of specimen storage locations. An operator can fill or empty the buffer specimen device with batches manually calmly and without disturbance so that work time is also saved. The comparatively slow individualization for the transfer and the transfer itself take place automatically independently of the work of the operator.

It is advantageous for optimizing the use of the device if the buffer specimen storage device to be used with a climatic cabinet is designed as a separate unit that can be detachably connected to the climatic cabinet via a coupling device.

The filling and emptying of the climatic cabinet is particularly simple due to the fact that the buffer specimen storage device comprises at least one specimen slide cassette, because the specimen slide cassette can be used independently of the climatic cabinet.

The above advantages are particularly advantageous because the buffer specimen storage device comprises several specimen storage cassettes in a carousel arrangement.

This carousel arrangement can basically be a rotary disk without a drive that is rotated by an operator into the desired position. It can be automatically actuated with a basically known carousel drive and control device.

The advantages of an automatic operating sequence are achieved in particular in that the outer transport device comprises a vertically movable lift and a horizontally movable shifting unit.

A temperature drop on the blade is minimized in that an intermediary repository for a specimen is located between the outer and the inner transport device in the vicinity of the transfer opening. Thus, the blade remains substantially in the area of the inner temperature and does not become warm during the transfer.

An especially advantageous further refinement of the invention consists in a climatic cabinet with several transfer openings by which correspondingly many specimen storage devices are loaded by several inner transport devices in that the outer transport device has an operative connection to all transfer openings. This has the advantage that even large-capacity climatic cabinets can be equipped and retrofitted in a simple manner.

In order to protect the specimen slides and to even better hinder icing, it is advantageous that the buffer specimen storage device and the outer transport device be arranged in a housing with a service opening. The housing functions as an air lock chamber. This applies in particular to a preferred further refinement in which a device is present for the pre-air-conditioning of the buffer specimen storage device and/or of the outer transport device. In this connection the term "air-conditioning" denotes at least a cooling or a heating. This has the advantage that the buffer specimen storage device can be used as a thawing station when removing objects from storage.

An especially simple and effective device for pre-air-conditioning is designed as a blower whose air flow is directed onto the buffer specimen storage device.

It is advisable during charging or removal that the pre-air-conditioning device be controlled as a function of an actuation of the service opening. In this manner the temperature in the housing can purposefully track and be held as constant as possible.

If the buffer specimen storage device together with the outer transport device and the housing are designed as a separate unit that can be detachably connected to the climatic cabinet via a coupling device, the possibilities of use are especially numerous.

BRIEF DESCRIPTION OF THE DRAWINGS

The invention is described further in the following using three exemplary embodiments shown in the drawings.

DETAILED DESCRIPTION OF THE INVENTION

Figure 1:
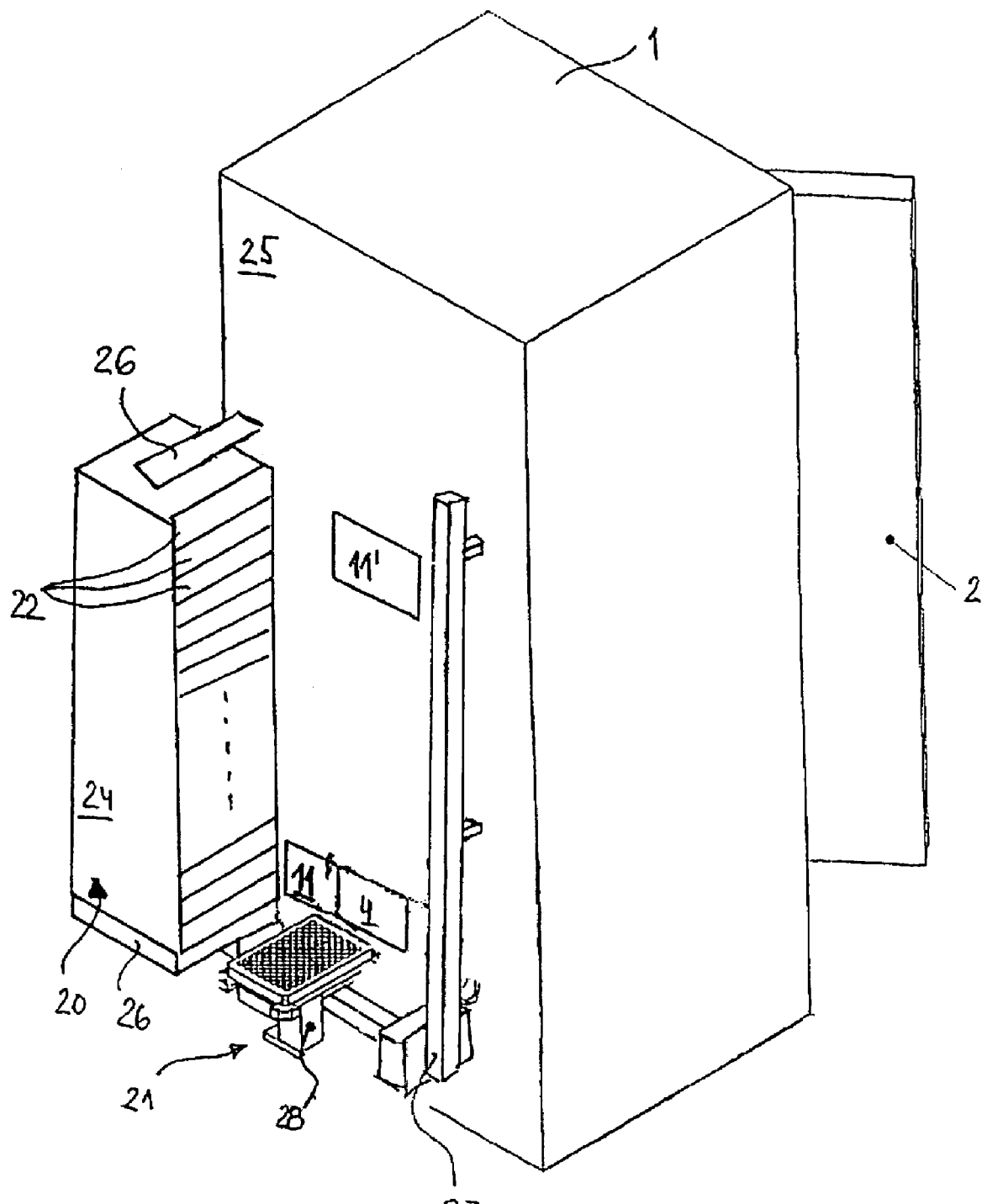
FIG. 1 shows a perspective of a first climatic cabinet.
Figure 2:
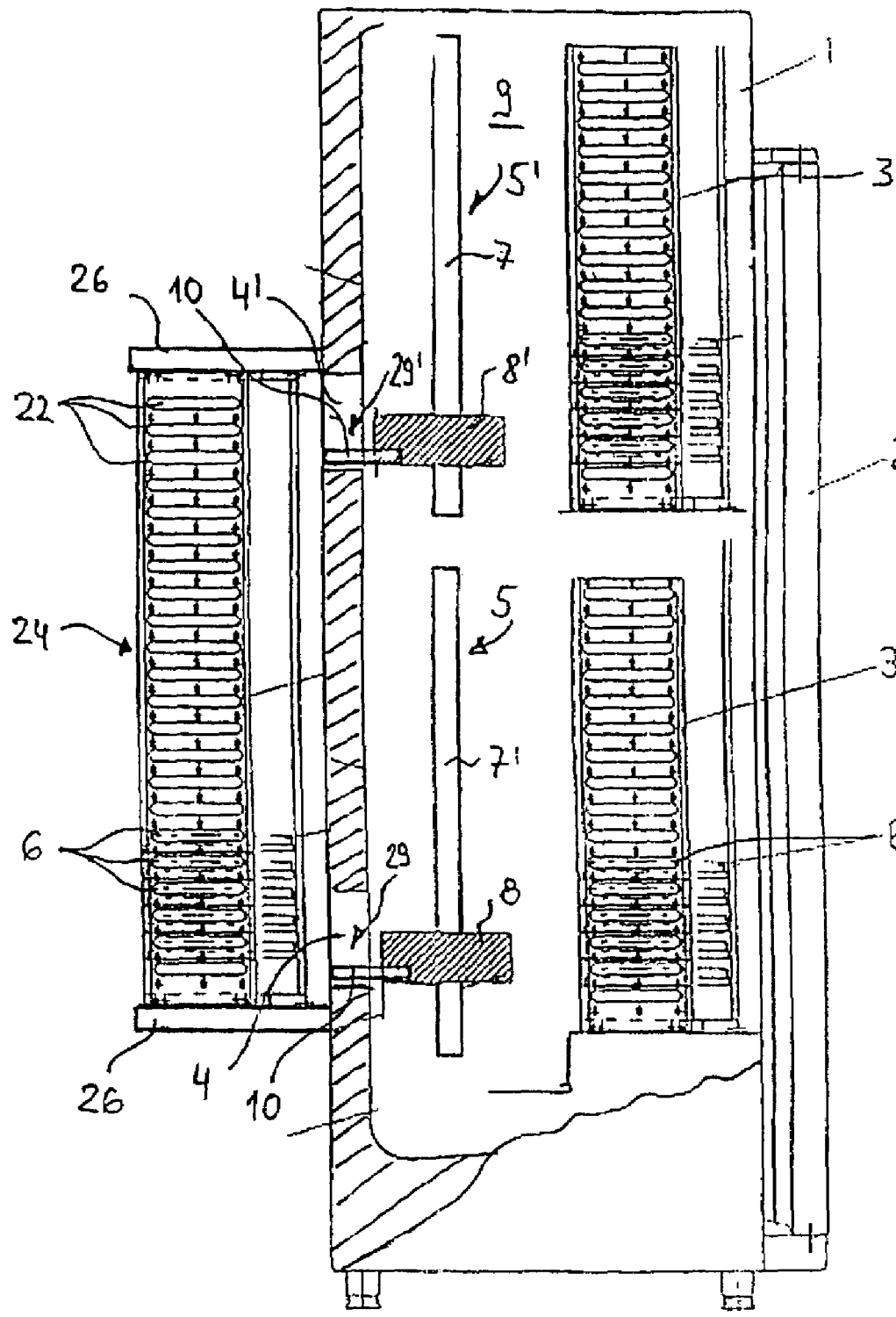
FIG. 2 shows a partial cross section through the first climatic cabinet according to FIG. 1 along section line II-II.

A first climatic cabinet 1 shown in FIG. 1 and FIG. 2 comprises a large-area door 2 to utilization space 9 through which two specimen storage stations 3, 3' superposed in the example shown can be installed and removed and through which maintenance work and the like is possible. In FIG. 1 door 2 is shown open for the sake of clarity whereas FIG. 2 shows the closed state. Two superposed and spaced transfer openings 4, 4' are present in the opposite wall of climatic cabinet 1 through which specimen slides 6 can be introduced into climatic cabinet 1 and into specimen storage stations 3, 3' and removed from them by two inner transport systems 5, 5'. Transfer openings 4, 4' can be closed by doors 11, 11'. Upper door 11' is closed and lower door 11 is open.

A buffer specimen storage device 20 is attached to the outside of the climatic cabinet and cooperates with outer transport device 21, also attached to the outside, in such a manner that a transport connection is established between the individual storage locations 22 of buffer specimen storage device 20 and transfer openings 4, 4'.

Outer transport device 21 transfers a specimen slide to one of inner transport devices 5, 5' at one of two transfer locations 23, 23' or receives a specimen slide there. Transfer locations 23, 23' are located in an area of transfer openings 4, 4' facing utilization space 9 behind the doors of transfer openings 4, 4'.

Buffer specimen storage device 20 is designed in the manner of a specimen slide cassette 24. Such specimen slide cassettes 20 are also designated as stackers. A plurality of specimen slides can be deposited in a superposed manner in buffer specimen storage device 20. A specimen slide cassette 24 consists substantially of a tower-shaped construction with two sidewalls 25 between which support positions 22 for specimen slides 6 are superposed like shelving. Typically, approximately 20 support positions are superposed within one specimen slide cassette 24. Specimen slides are drawn out or inserted via an open side of specimen slide cassette 24 by outer transport device 21.

Specimen slide cassette 24 can be permanently connected to the wall of climatic cabinet or, as in the exemplary embodiment, be held detachably as a separate unit in holder 26 on the wall of climatic cabinet 1. In this instance it can be a commercial specimen slide cassette 24.

Buffer specimen storage device 20 is filled or emptied by an operator manually, which can take place on site or, in the case of a specimen slide cassette 24 designed as an independent unit, at some other location in order to be inserted, filled or emptied into holder 26.

Outer transport device 21 comprises lift 27 and horizontal shifting unit 28 arranged on it with a grasper or the like for the vertical and horizontal transport of a specimen slide between storage positions 26 and transfer openings 4, 4'. Accordingly, the displaceability in height of lift 27 and the range of horizontal shifting unit 28 are selected in such a manner that both transfer openings 4, 4' can be reached.

Each of inner transport devices 5, 5' is basically designed in the same manner with another lift 7, 7' and horizontally movable shifting devices 8, 8'. A blade 10, 10' that receives the slide during transport is present on each horizontal shifting device 8, 8'.

Slide storage devices 3, 3' can comprise several slide cassettes 24', e.g., arranged as a carousel or in series. In order to keep the figure easy to understand, only one specimen slide cassette 24' is shown.

A typical operation develops in the following manner. A certain number of storage places of specimen storage devices 3, 3' are covered with specimen slides 6 and utilization space 9 is brought to a temperature of approximately −20° C. Other specimen slides 6 are present in buffer specimen storage device 20 at room temperature. A specimen slide to be removed is taken from its specimen slide cassette 24' by blade 10 under the control of an automatic control unit (not shown) and brought to transfer location 23 via lift 7 and horizontal shifting unit 8. Outer transport device 21 moves from the outside under automatic control in front of the door of the briefly opened particular transfer opening 4 in order to be able to take the slide from blade 10. After outer transport device 21 has moved out of transfer opening 4, the door is closed again so that the blade was only briefly exposed to the outer temperature. Outer transport device 21 deposits the slide by means of lift 27 and horizontal sliding device 28 in a storage location of specimen slide cassette 24 where it is removed by an operator. A filling of the climatic cabinet takes place in the inverse sequence.

Figure 3:
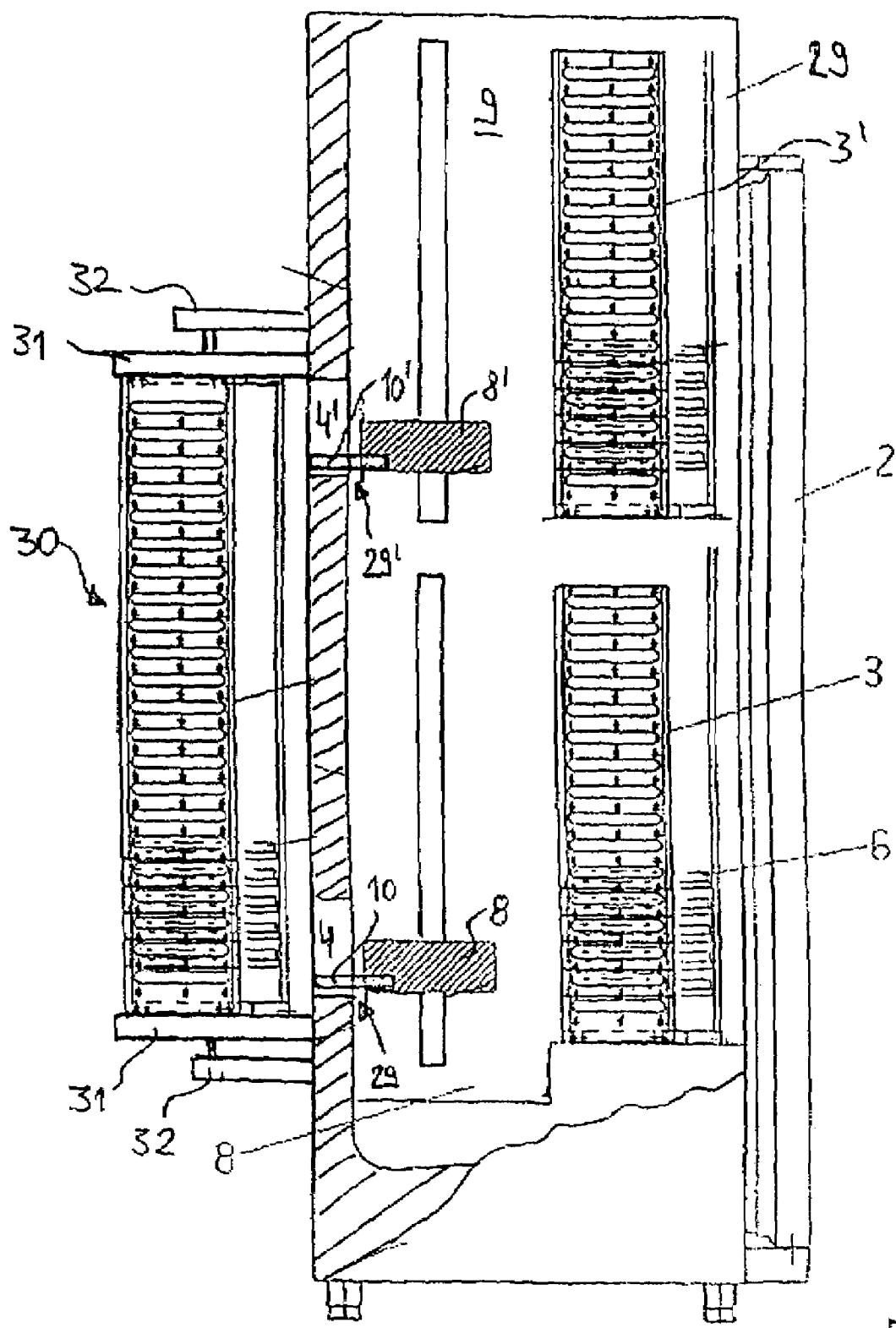
FIG. 3 shows a partial cross section through a second climatic cabinet.

The exemplary embodiment of a second climatic cabinet 29 according to FIG. 3 differs from the first climatic cabinet 1 in that buffer specimen storage device 30 has a plurality of specimen slide cassettes 24 instead of a single specimen slide cassette 24 that are arranged in a stellate manner in the manner of a carousel on rotary disk 31 functioning as cassette carrier in such a manner that their open sides face outward for the placing and removal of specimen slides 24. The desired specimen slide cassette 24 is moved to the outer transport device by rotating rotary disk 31 and aligned, which transport device can access a storage location in a purposeful manner via its height-adjustable grasper. For its part, rotary disk 31 is held by rotary-disk support 32 on the wall of second climatic cabinet 29. Specimen slide cassettes 24 are removably held on rotary disk 31.

Figure 4:
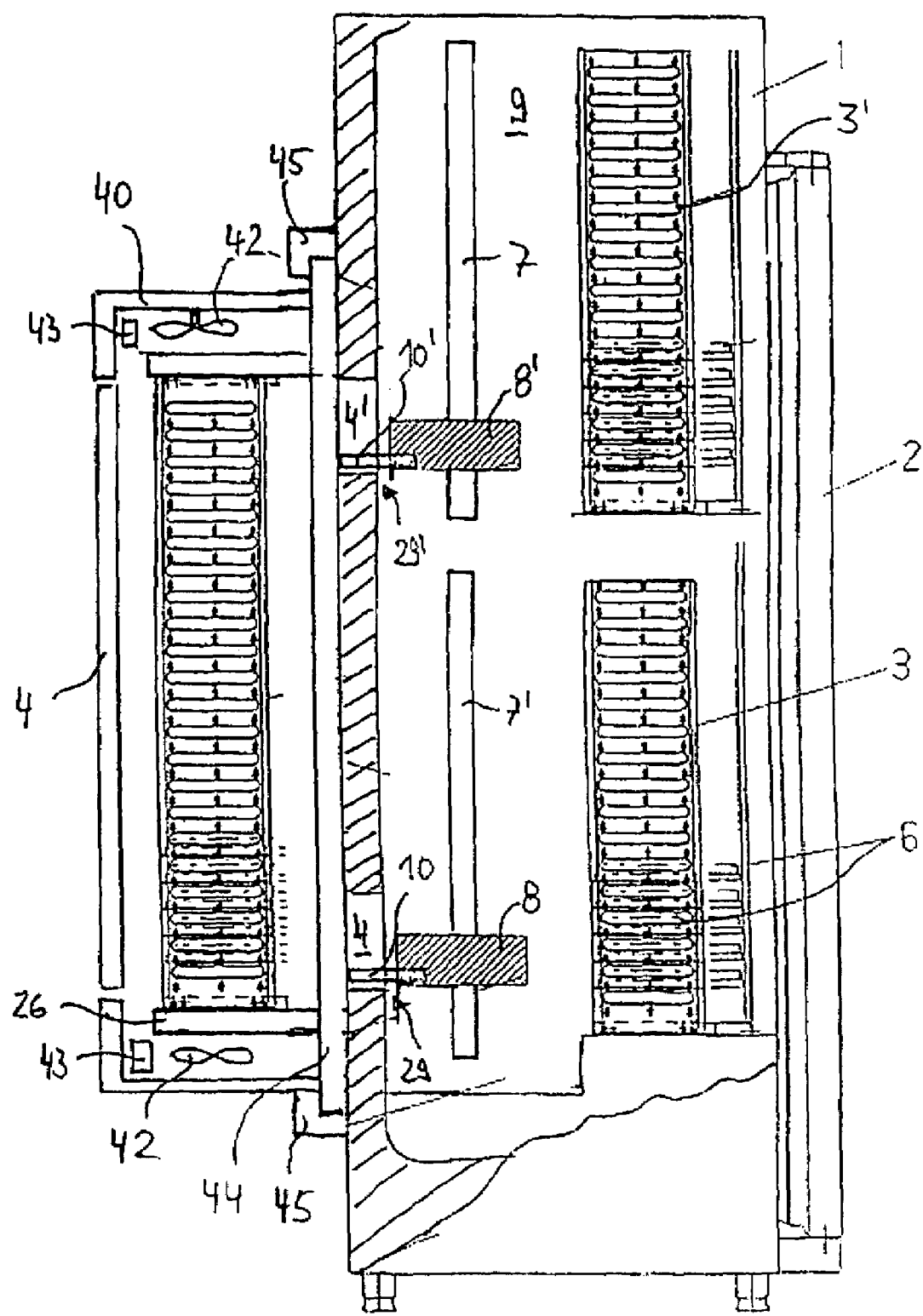
FIG. 4 shows a partial cross section through a third climatic cabinet.

According to FIG. 4 a housing 40 is placed around buffer specimen storage device 20 and outer transport device 21. It has a service door 41 for filling and emptying buffer specimen storage device 20 by an operator. Cooling air or air heated by heating device 43 can be directed onto buffer specimen storage device 20 by blower 42 in order to pre-cool or thaw specimen slides 6 placed in it.

Blower 42 and heating device 43 can be turned on and off manually but are preferably controlled by a thermostat or turned on and off automatically as a function of whether service door 41 is open or closed.

FIG. 4 also shows that housing 40, buffer specimen storage device 20 and outer transport device 21 are arranged on a common base 44 detachably fastened by coupling device 45 to the wall of third climatic cabinet 50.

For the rest, the parts that are the same as in FIG. 1 are provided with the same reference numerals.

The invention claimed is:
1. A climatic cabinet, comprising:
   a plurality of walls defining a utilization space, one wall having at least one transfer opening with a respective door, the transfer opening providing access to the utilization space;
   at least one specimen storage device, disposed within the utilization space, including a plurality of storage locations;
   at least one inner transport device, disposed within the utilization space, to transport specimen slides to and from the specimen storage device;
   a buffer specimen storage device, disposed outside the utilization space, including a plurality of storage locations;

and an outer transport device, disposed outside the utilization space, to transport specimen slides to and from the buffer specimen storage device and to establish a transport connection with the transfer opening such that a specimen slide is transported between the buffer specimen storage device, the inner transport device, and the specimen storage device.

2. The buffer specimen storage device for use with a climatic cabinet in accordance with claim 1, wherein the buffer specimen storage device is designed as a separate unit that can be detachably connected via a coupling device to the climatic cabinet.

3. The climatic cabinet according to claim 1, wherein the buffer specimen storage device comprises at least one specimen slide cassette.

4. The climatic cabinet according to claim 2, wherein the buffer specimen storage device comprises several specimen storage cassettes in a carousel arrangement.

5. The climatic cabinet according to claim 1, wherein the outer transport device comprises a vertically movable lift and a horizontally movable shifting unit.

6. The climatic cabinet according to claim 1, wherein the transfer location for a specimen is located between the outer and the inner transport device in the area of the transfer opening.

7. The climatic cabinet according to claim 1, including a plurality of transfer openings by which a plurality of specimen storage devices are loaded by a plurality of inner transport devices, wherein the outer transport device has an operative connection to the transfer openings.

8. The climatic cabinet according to claim 1, wherein the buffer specimen storage device and the outer transport device are arranged in a housing with a service opening.

9. A buffer specimen storage device with an outer transport device and housing for use with a climatic cabinet according to claim 8, wherein the buffer specimen storage device is designed as a separate unit that can be detachably connected to the climatic cabinet via a coupling device.

10. The climatic cabinet according to claim 1, wherein a device is present for the pre-air-conditioning of the buffer specimen storage device and/or of the outer transport device.

11. The climatic cabinet according to claim 1, wherein the device for pre-air-conditioning is designed as a blower.

12. The climatic cabinet according to claim 1, wherein the device for pre-air-conditioning is controlled as a function of an actuation of the service opening.

13. A climatic cabinet, comprising:
a plurality of walls defining a utilization space, one wall having a closable transfer opening providing access to the utilization space;
a first means for storing specimen slides, disposed within the utilization space;
a first means for transporting specimen slides, disposed within the utilization space, to convey specimen slides between the first means for storing and the transfer opening;
a second means for storing specimen slides, disposed outside the walls; and
a second means for transporting specimen slides, disposed outside the walls, to convey specimen slides between the second means for storing and the transfer opening, the first and second means for transporting cooperating together to exchange specimen slides within the transfer opening.

14. The climatic cabinet according to claim 13, wherein the second means for storing is detachably connected to the wall having the transfer opening.

15. The climatic cabinet according to claim 13, wherein the second means for storing is a specimen slide carousel.

16. The climatic cabinet according to claim 13, wherein the second means for storing and the second means for transporting are disposed within a housing having a service opening.

17. The climatic cabinet according to claim 16, further including a means for temperature conditioning the specimen slides disposed within the housing.

18. The climatic cabinet according to claim 13, wherein the second means for transporting includes a vertically-movable lift and a horizontally-movable shifting unit.

19. The climatic cabinet according to claim 13, wherein the wall has a plurality of transfer openings through which the specimen slides are exchanged.

* * * * *